(12) United States Patent
Eibl et al.

(10) Patent No.: US 7,771,197 B2
(45) Date of Patent: *Aug. 10, 2010

(54) DENTAL HANDPIECE WITH A ROOT CANAL LENGTH MEASUREMENT FUNCTION

(75) Inventors: Johann Eibl, Mattighofen (AT); Andreas Brandstaetter, St. Pantaleon (AT)

(73) Assignee: W & H Dentalwerk Bürmoos GmbH, Bürmoos (AT)

( * ) Notice: Subject to any disclaimer, the term of this patent is extended or adjusted under 35 U.S.C. 154(b) by 0 days.

This patent is subject to a terminal disclaimer.

(21) Appl. No.: 12/228,406

(22) Filed: Aug. 11, 2008

(65) Prior Publication Data

US 2009/0047616 A1 Feb. 19, 2009

Related U.S. Application Data

(63) Continuation of application No. 11/239,956, filed on Sep. 29, 2005, now Pat. No. 7,452,208.

(30) Foreign Application Priority Data

Sep. 30, 2004 (EP) .................................. 04023260

(51) Int. Cl.
*A61C 19/04* (2006.01)
*A61C 3/00* (2006.01)
(52) U.S. Cl. ............................... 433/72; 433/27; 433/75
(58) Field of Classification Search .................. 433/27, 433/72, 75, 98–99, 102, 29; 600/589–590
See application file for complete search history.

(56) References Cited

U.S. PATENT DOCUMENTS 3,745,654 A 7/1973 Ellman
(Continued)

FOREIGN PATENT DOCUMENTS

DE 195 20 765 12/1995
(Continued)

OTHER PUBLICATIONS

Office Action from the United States Patent & Trademark Office in co-pending U.S. Appl. No. 11/239,956, dated Aug. 3, 2007.
(Continued)

*Primary Examiner*—Cris L Rodriguez
*Assistant Examiner*—Heidi M Eide
(74) *Attorney, Agent, or Firm*—Klarquist Sparkman, LLP

(57) ABSTRACT

A handpiece for measuring root canal length having an outer sleeve that is substantially non-insulating, a connecting device, an instrument carrier, at least one transmission element within the outer sleeve, a length measuring circuit portion, a contact portion and an insulating portion. The instrument carrier is configured to receive a dental instrument. The transmission element transmits force to move the instrument carrier so that a dental instrument received in the instrument carrier executes a rotating, reciprocating and/or vibrating working movement. The length measuring circuit portion is disposed inside the handpiece and operable to transmit measuring signals for measuring length. The contact portion is operable to establish a conductive path between the dental instrument serving as an electrode and the length measuring circuit portion. The insulating portion insulates the length measurement circuit portion and the contact device, through which a voltage is applied during measurement, from the outer sleeve.

27 Claims, 3 Drawing Sheets

U.S. PATENT DOCUMENTS

| | | | |
|---|---|---|---|
| 4,243,388 | A | 1/1981 | Arai |
| 5,897,315 | A | 4/1999 | Nakayama et al. |
| 5,902,105 | A | 5/1999 | Uejima et al. |
| 6,053,732 | A | 4/2000 | Sale |
| 7,070,411 | B2 | 7/2006 | Nakanishi et al. |

FOREIGN PATENT DOCUMENTS

| | | |
|---|---|---|
| DE | 197 02 370 | 8/1997 |
| EP | 1 444 966 | 8/2004 |

OTHER PUBLICATIONS

Office Action from the United States Patent & Trademark Office in co-pending U.S. Appl. No. 11/239,956, dated Dec. 17, 2007.

Office Action from the United States Patent & Trademark Office in co-pending U.S. Appl. No. 11/239,956, dated Mar. 14, 2008.

DENTAL HANDPIECE WITH A ROOT CANAL LENGTH MEASUREMENT FUNCTION

CROSS REFERENCE TO RELATED APPLICATION

The present application is a continuation of U.S. patent application Ser. No. 11/239,956, filed Sep. 29, 2005, now U.S. Pat. No. 7,452,208 and claims priority from pending European Patent Application No. 04023260.5, filed Sep. 30, 2004, which are hereby incorporated herein by reference.

BACKGROUND

1. Field

The present application concerns a dental handpiece for the treatment of root canals and the measurement of the root canal length.

2. Description of Prior Art

Such a handpiece is part of a device for the determination of the length (depth) of a root canal and of the position of the treatment instrument attached to the handpiece, respectively. The device comprises, together with the handpiece, two electrodes and a control and evaluation unit. The first electrode, usually in the form of a clip-on electrode, is attached to the oral mucosa of the patient. The instrument attached to the handpiece, for example a file moving back and forth (executing reciprocating movements), a reamer or a rotating dental drill, serves as the second electrode. Both electrodes are connected to the control and evaluation unit. The control and evaluation unit is connected to a current source, which generates a measuring signal, and furthermore includes a measuring device, preferably a measuring circuit, which determines the length of the root canal and the position of the dental instrument, respectively, on the basis of the change in the electrical resistance or the change in the impedance of the measuring signal between the two electrodes.

From EP 1 444 966 A1, a handpiece is known with which the signal line is implemented by a conducting wire outside of the handpiece, the wire being connected to the dental instrument, serving as the second electrode, with a clip-on connection and a clip holder. The disadvantage with this arrangement is the conducting wire is attached to the sleeve of the handpiece handle, which restricts the manageability of the handpiece.

In order to avoid this disadvantage, handpieces are manufactured with which conductors or components of the handpiece implement the signal line within the handpiece. DE 197 02 370 A1 (DE '370 A1) discloses an arrangement of conducting wires within the handpiece or in the sleeve of the handpiece which make contact with the instrument serving as an electrode by way of a contact device. In the DE 195 20 765 A1 (DE '765 A1) components serving for the transmission of the drive power, especially shafts and gears, parts of the outer sleeve and components in contact with these components are used for signal transmission.

With both designs, it is necessary that at least parts of the outer sleeves are insulated in order to prevent the impairment of the measuring circuit due to contact between the handpiece and the oral cavity of the patient or the hand of the user. Insulation may be achieved by manufacturing part of the handle from plastic, as seen in the DE '370 A1. Alternatively, an insulating film can be attached to the outer surface of the outer sleeve, as explained in connection with the DE '765 A1.

These known handpieces have the disadvantage on the one hand of the greater manufacturing costs due to the coating and on the other hand that plastics used for coating or as a material for the handle sleeve sections are not stable relative to the prevailing ambient conditions for sterilization, particularly steam-sterilization. Since however the handpieces must be sterilized following each use, the life of such coatings or handle sleeve sections is very limited.

The present application is therefore in response to the need for a dental handpiece for the treatment of root canals and the measurement of the root canal length while at the same time avoiding the disadvantages discussed above. In particular, the handpiece must be insensitive to the prevailing ambient conditions for sterilization.

SUMMARY

In the present application, the outer sleeve of the handpiece described below is comprised of non-insulating, preferably metallic, material and also has substantially no insulating coating. In relation to the prevailing ambient conditions for sterilization, it is therefore insensitive. Furthermore, to ensure faultless measurement of the root canal length and signal line integrity, all components of the handpiece which are part of the device for the transmission of the measuring signals or the contact device, and therefore "live," are insulated from the outer sleeve by insulating material. The components which establish a conductive path between the device for the transmission of the measuring signals and the instrument serving as electrode are part of the contact portion.

Parts of the contact device may also be disposed outside of the handpiece. In particular, this is necessary when a dental instrument having a non-conductive shaft is used. Such an instrument, for example a file, is comprised of a metallic—and thus conductive—working area and a shaft attached to this, which is at least partly surrounded (especially in the area in which the spindle is connected to the instrument carrier of the handpiece) by a plastic sleeve. In order to establish a connection between the conductive section of the dental instrument and the device for the transmission of the measuring signals, a contact device is required which makes physical contact with the dental instrument outside of the handpiece.

The same components are numbered identically in all figures.

DETAILED DESCRIPTION

Figure 1:
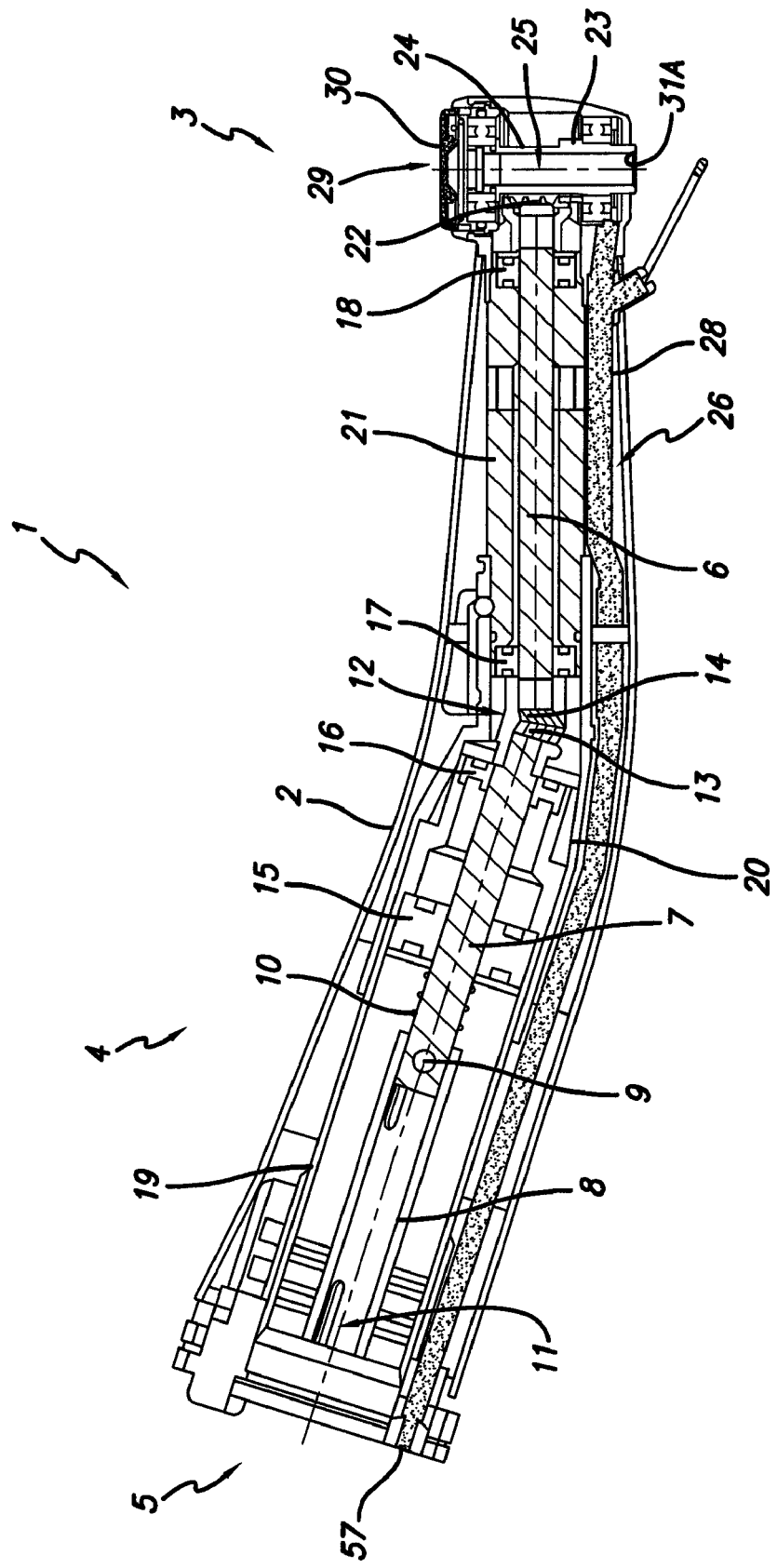
FIG. 1 shows a sectional view of a first embodiment for the handpiece.

The contra-angle handpiece 1 illustrated in FIG. 1 is comprised of an outer sleeve 2 with a head section 3 and a handle section 4. The entire outer sleeve 2 (including pushbutton 29) is not insulating, i.e. it is made substantially of a non-insulating, preferably metallic, material and also has substantially no insulating coating. At the proximal end of the outer sleeve 2 is a connecting device 5 for coupling the handpiece to a control and evaluation unit, a measuring circuit with a current source for the measurement of the root canal length and drive unit. The connecting device 5 is preferably designed in the form of the twist-on connection familiar to dental specialists, so that no further description is necessary here.

As used herein, the terms "non-conductive," "insulating" and "insulated" mean that the component or material so described reduces or prevents the transmission of electricity. Conversely, the terms "conductive," "conducting" and "non-insulating" mean that the component or material so described has the quality of conducting electricity. As would be understood by those of ordinary skill in the art, these terms are used to describe relative rather than absolute qualities.

The inside of the handle section 4 is interspersed with several elements for the transmission of the drive movement, including a first spindle designated the central drive spindle 6, a second spindle designated the drive spindle 7, and a hollow spindle 8. The drive spindle 7 is received by the distal end of the hollow spindle 8 and fixed by a straight grooved pin 9. A spring 10 preloads the hollow spindle 8 against the drive spindle 7 and allows an axial play of hollow spindle 8 relative to drive spindle 7. At the proximal end, the hollow spindle 8 is detachably connected by a carrier 11 to the rotating spindle of the drive unit, preferably an electrical motor.

The first spindle 6 and second spindle 7 are connected through a gear unit 12, consisting of two gearwheels 13, 14 pressed onto the two spindles 6, 7 and supported by several rolling bearings 15, 16, 17, 18 in the coupling and bearing sleeves 19, 20, 21. The rolling bearings 15, 16, 17, 18 are pre-stressed by spring washers, as illustrated by way of example for the bearing 18 in FIG. 2. Here, the spring washer 56 is mounted in an annular groove of the spacer disk 55. Another gear wheel 22 is pressed onto the distal end of the first spindle 6, which meshes with a gear wheel 23, connected to a hollow spindle, designated the head spindle 24. The head spindle 24 is simultaneously part of the instrument carrier 25, which detachably receives a dental instrument in the known manner. The rotary motion of the drive device is thus transmitted via the elements for the transmission of the drive movement 6, 7, 8 to the head spindle 24, the instrument carrier 25 and the dental instrument, preferably a rotating dental drill. Instead of the gear wheels 22, 23 of course an eccentric gear can be placed between the first spindle 6 and the head spindle 24, so that the dental instrument, preferably a file, executes stroke (reciprocating) movements.

A pushbutton 29, the cover 30 of which is pre-stressed by a spring 31 and the inside of which is provided with wedges 36 (FIG. 2), is provided for releasing the dental instrument from the instrument carrier 25. Pressing the pushbutton cover 30 in the direction of the opening 31A of the instrument carrier 25 up to the collar 32 of the supporting ring 33 moves the cylindrical slider 34, pre-stressed by another spring 35, radially through the wedges 36 (to the right in FIG. 2) until it is positioned coaxially with the instrument carrier 25 and the user can remove the dental instrument from the instrument carrier 25.

The inside of the handpiece 1 also has a device 26 for the transmission of the measuring signal for the length measurement. For the handpiece 1 illustrated in FIG. 1, the device 26 is formed by a conducting wire 27, to which a voltage is applied while performing the length measurement and which is surrounded by a casing 28 of insulating material, in particular plastic. The proximal end of the conducting wire 27 in the region of the connecting device 5 is in the form of the sliding contact 57, which is joined through the connecting device 5 to a slip ring of the connecting element, for example the drive unit or a coupling. If the connecting device 5 is a non-rotating plug-in connector, the proximal end of the conducting wire 27 is in the form of a contact pin to be seated in a socket connector of the connecting element coupled to the handpiece 1.

The distal end of the connecting wire 27 is split into two ends, 27A and 27B. At each of the two ends 27A, 27B is a contact device 37A, 37B, respectively, which establishes a conductive path between the dental instrument serving as electrode and the connecting wire 27. The contact device 37 B is intended for dental instruments having a non-conductive section and is in the familiar U-shaped form, comprising an elastic wire 38 with two legs 39 (in the sectional view only one leg can be seen). In the frontal end region both legs 39 are curved inward. This curvature region is essentially under the opening 31 of the instrument carrier 25, so that a dental instrument placed in the instrument carrier 25 runs between the two legs and makes physical contact on two sides of the legs 39.

The base 40 of the U-shaped wire 38 is connected to a sleeve 41, preferably using a terminal connection. At one end, the sleeve 41 has a flange 42 attached, preferably by a cement bond, to the inside of the outer sleeve 2. A stem 43 of the sleeve 41 projects outwards through a bore 44 in the outer sleeve 2, with the diameter of the bore 44 smaller than that of the flange 42. The sleeve 41 on the end opposite the flange 42 has a groove 45 with two ledges 46 and 47, with the diameter of the groove 45 smaller than the diameter of the base 40 of the U-shaped wire 38. Since the side walls of the groove 45 have a slight spring mounting, when the user applies pressure while connecting the base 40 to the ledges 46, 47 they are pushed aside, so that the base 40 reaches the connective region 45A of the groove 45 and is fixed by the ledges 46, 47 returning as a result of the spring mounting to their original positions. To disconnect the base 40, the user pulls on the U-shaped wire 38, causing the ledges 46, 47 to again move aside and release the base 40.

The end 27B of the connecting wire 27 is received inside the sleeve 41 and makes contact with the base 40 of the U-shaped wire 38 clamped in the section 45A of the groove 45, so that a conductive path is established between the dental instrument serving as electrode, the legs 39 and the base 40 of the wire 38, the end 27B and the connecting wire 27 to the sliding contact 57.

In order to prevent disturbances in the measuring and signal wire, the sleeve 41 should be in the form of an insulating element, i.e. made of non-conductive material, preferably plastic, or coated with plastic. It is of course possible to use a separate component made of conductive material, for example a spring or a flexing element making contact with the connecting wire 27, in place of the end 27B of the conducting wire.

When using a dental instrument consisting entirely of a conductive material, the user may disconnect the wire 38 from the sleeve 41. In this case, the contact device 37A with the end 27A of the connecting wire 27 serves to connect the dental instrument to the sliding contact 57. The end 27A makes contact with the outer ring 48A of the spring washer 48 via a bore 54 in the socket 49. The spring washer 48 in turn makes a sliding contact with the head spindle 24, as part of the instrument carrier 25, and the dental instrument attached. A voltage is applied to the spring washer 48 with outer ring 48A and head spindle 24 while executing the measurement of the root canal length. The spring washer 48 is bearing-mounted in the socket 49 and serves for the pre-stressing of the rolling bearing 50, which is pressed onto the head spindle 24 and supports the head spindle 24 rotatably. A second rolling bearing 51 is analogously arranged on the pushbutton side of the head spindle 24 and fixed by an O-ring 52, which is bearing-mounted in a ring groove 53 of the supporting ring 33. As the sliding contact between the head spindle 24 and the connecting wire 27 other elements, such as a brush or a contact pin, can also be used.

In order to ensure fault-free measurement of the root canal length and signal transmission through the contact device 37A, at least the following components must serve as insulating means, i.e. must be made of non-conductive material: the socket 49, the supporting ring 33 and the gearwheel 22 and/or 23. To obtain better insulation of the outer sleeve 2, in a preferred embodiment, in addition one or more of the rolling bearings 18, 50, 51 and/or the spacer disk 55 and/or the first spindle 6 should be made of insulating, i.e. non-conductive, material. In another embodiment, the first spindle 6 is comprised of several spindle sections, at least one of which is in the form of a non-conductive, insulating element.

The materials used for the components serving as the insulating portion are in particular plastic, preferably PEEK (polyetheretherketone) or silicone, or ceramic materials. Coatings with these materials applied to the components serving as the insulating means also ensure sufficient insulation. Preferably, the raceways and/or the rolling elements of the rolling bearings 18, 50, 51 are made of ceramic materials, such as silicon nitride, zirconium nitride or silicon carbide. The gearwheel 22, the supporting ring 33, the socket 49 and at least part of the first spindle 6 and spacer disk 55 are preferably made of plastic.

A handpiece can of course be equipped with only a contact device 37A or 37B as well, however it is advantageous to implement both contact devices 37A and 37B in the handpiece, since this handpiece 1 may then be used with dental instruments having an insulated instrument shaft as well as those not having an insulating instrument shaft.

Figure 3:
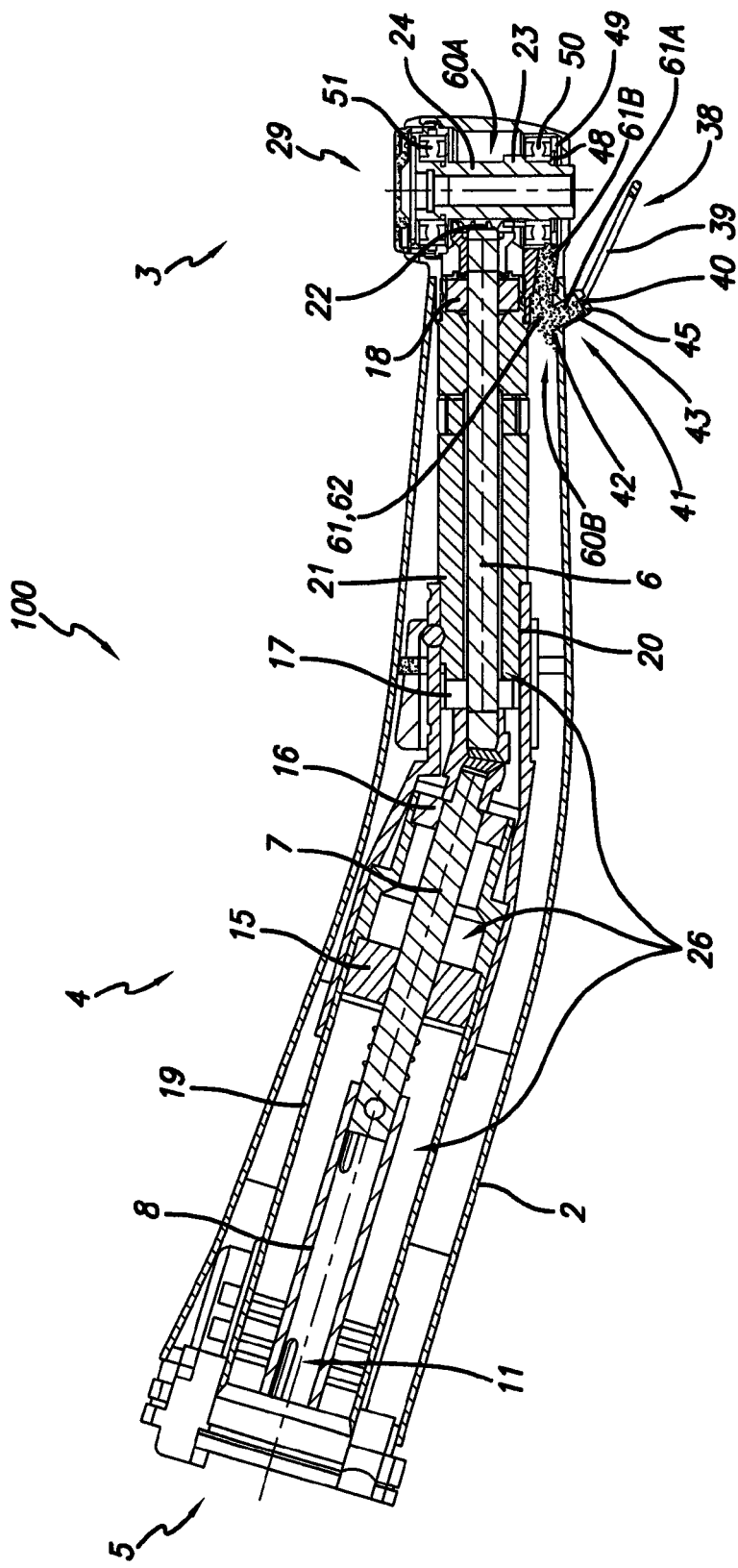
FIG. 3 shows a sectional view of a second embodiment for the handpiece.

The handpiece 100 shown in FIG. 3 in principle has the same design as handpiece 1, so that it is not necessary to repeat the detailed description. The entire outer sleeve 2 with handle section 4 and head section 3 (including pushbutton 29) is once again made of completely non-insulating, preferably metallic, material and has no insulating coating.

Figure 2:
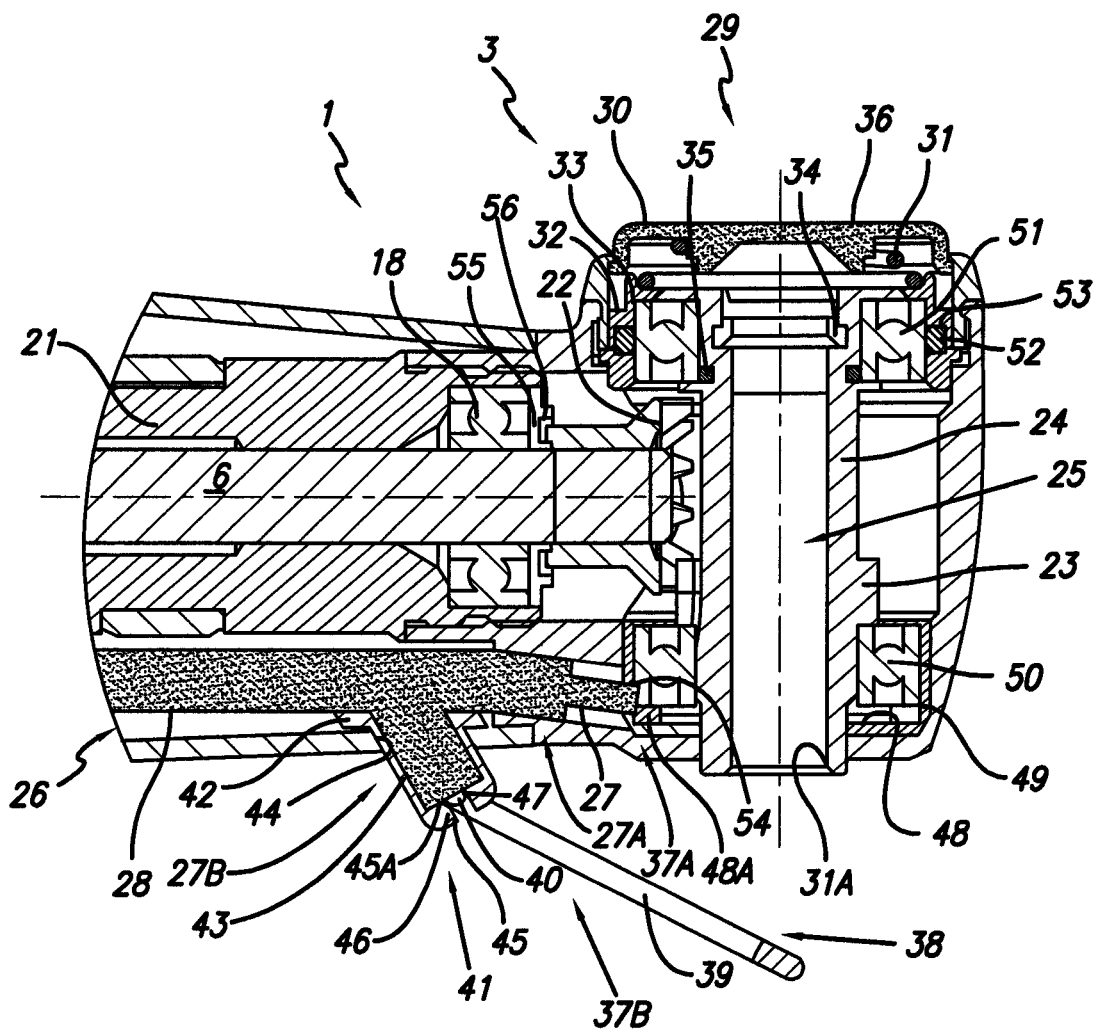
FIG. 2 shows the head of the handpiece in FIG. 1 on an enlarged scale.

With the handpiece 100, the device for the transmission of the measuring signal 26 for the determination of the root canal length consists of the elements for the transmission of the drive movement (first spindle 6, second spindle 7, hollow spindle 8). A voltage is applied to these elements while executing the measurement of the root canal length, which must therefore be made of conductive material. For dental instruments with a conductive section, the head spindle 24 with gearwheel 23 and gearwheel 22 serve as the contact device 60A with applied voltage. For dental instruments with a non-conductive section of the instrument shaft, the contact device 60B must be used in order to establish a conductive path of the dental instrument with the elements 6, 7, 8 for the transmission of the drive movement via the head spindle 24 and the gearwheels 22, 23. The contact device 60B consists of a U-shaped elastic wire 38, connected through its base 40 to the sleeve 41, preferably using a terminal connection, and a conducting wire 61 with a first end 61A and a second end 61B. The first end 61A is taken up in the sleeve-shaped stem 43 of the sleeve 41, which makes contact with the base 40 of the U-shaped wire 38, clamped in section 45A of the groove 45. The second end 61B of the conducting wire 61 is connected through the bore 54 of the socket 49 to the outer ring 48A of the spring washer 48 (FIG. 2). Via the sliding contact between the spring washer 48 and the head spindle 24, as part of the instrument carrier 25, a connection is established through the gearwheels 22, 23 to the elements for the transmission of the drive movement 6, 7, 8.

The retransmission of the measuring signals takes place from the hollow spindle 8, via the driver 11 to the connecting piece coupled to the handpiece 100 through the connecting device 5, for example the rotor shaft of the drive unit or the shaft of a coupling.

In order to ensure fault-free measurement of the root canal length and signal transmission through the contact device 60A, at least the following components should be insulating, i.e., must be made of non-conductive material: the supporting ring 33 and the socket 49. When using the contact device 60B, in addition the sleeve 41 should be in the form of an insulating material. Preferably, the conducting wire 61 is also surrounded by an insulating sheath 62. To obtain better insulation of the head section 3 of the outer sleeve 2, in another preferred embodiment, in addition one or more of the rolling bearings 50, 51 should be made of insulating, i.e. non-conductive, material.

To insulate the handle section 4 of the outer sleeve 2, at least the rolling bearings 15, 16, 17, 18 should be in the form of insulating means. Preferably, one or more of the coupling and bearing sleeves 19, 20, 21 are also made of non-conductive material. The materials for the components comprising the insulating portion are the same as described for handpiece 1.

The invention is not limited to the embodiments discussed above, but encompasses all embodiments which do not change the fundamental functional principle of the invention. In particular, the handpiece according to the invention for the measurement of the root canal length does not depend on the type of drive unit and includes pneumatic, piezoelectric or magnetostrictive vibration drives as well. Depending on the type of drive unit, the elements for the transmission of the drive movement to the instrument carrier are different in form and can, for example, also include or vibrating rods or flexible spindles.

What is claimed is:

1. A handpiece for measuring root canal length, comprising:
    an outer sleeve that is substantially non-insulating and is substantially free of any insulating coating,
    a connecting device for coupling the handpiece to a control and evaluation unit, to a measuring circuit with a current source for measurement of root canal length and to a drive unit,
    an instrument carrier configured to receive a dental instrument,
    at least one transmission element within the outer sleeve that transmits force to move the instrument carrier so that, when received in the instrument carrier, the dental instrument executes a rotating, reciprocating and/or vibrating working movement,
    a length measuring circuit portion disposed inside the handpiece and operable to transmit measuring signals for measuring length,
    a contact portion operable to establish a conductive path between the dental instrument serving as an electrode and the length measuring circuit portion, and
    an insulating portion that insulates the length measurement circuit portion and the contact portion, through which a voltage is applied during measurement, from the outer sleeve,
    wherein the outer sleeve does not conduct electricity during measurement, and
    wherein the length measuring circuit portion comprises the at least one transmission element and the insulating portion comprises at least one non-conductive rolling bearing positioned between the at least one transmission element and the outer sleeve.

2. The handpiece of claim 1, wherein the length measuring circuit portion comprises a conducting wire and the insulating portion comprises a wire sheath of non-conductive material.

3. The handpiece of claim 1, wherein the contact portion comprises a contact device for use with a dental instrument having a conductive shaft, the contact device establishing a connection between the dental instrument and the length measuring circuit portion.

4. The handpiece of claim 1, wherein the insulating portion comprises a plastic material such as PEEK or silicone, or a ceramic material such as silicon nitride, zirconium nitride or silicon carbide, or a coating comprised of said plastic material and/or said ceramic material.

5. The handpiece of claim 1, wherein the outer sleeve is made of a metallic material.

6. A handpiece for measuring root canal length, comprising:
- an outer sleeve that is substantially non-insulating and is substantially free of any insulating coating,
- a connecting device for coupling the handpiece to a control and evaluation unit, to a measuring circuit with a current source for measurement of root canal length and to a drive unit,
- an instrument carrier configured to receive a dental instrument,
- at least one transmission element within the outer sleeve that transmits force to move the instrument carrier so that, when received in the instrument carrier, the dental instrument executes a rotating, reciprocating and/or vibrating working movement,
- a length measuring circuit portion disposed inside the handpiece and operable to transmit measuring signals for measuring length,
- a contact portion operable to establish a conductive path between the dental instrument serving as an electrode and the length measuring circuit portion, and
- an insulating portion that insulates the length measurement circuit portion and the contact portion, through which a voltage is applied during measurement, from the outer sleeve,
- wherein the outer sleeve does not conduct electricity during measurement, and
- wherein the insulating portion includes at least one of a coupling sleeve, a bearing sleeve and a spacer disk.

7. The handpiece of claim 6, wherein the length measuring circuit portion comprises a conducting wire and the insulating portion comprises a wire sheath of non-conductive material.

8. The handpiece of claim 6, wherein the length measuring circuit portion comprises the at least one transmission element.

9. The handpiece of claim 6, wherein the insulating portion comprises a plastic material such as PEEK or silicone, or a ceramic material such as silicon nitride, zirconium nitride or silicon carbide, or a coating comprised of said plastic material and/or said ceramic material and wherein the outer sleeve is made of a metallic material.

10. A handpiece for measuring root canal length, comprising:
- an outer sleeve that is substantially non-insulating and is substantially free of any insulating coating,
- a connecting device for coupling the handpiece to a control and evaluation unit, to a measuring circuit with a current source for measurement of root canal length and to a drive unit,
- an instrument carrier configured to receive a dental instrument,
- at least one transmission element within the outer sleeve that transmits force to move the instrument carrier so that, when received in the instrument carrier, the dental instrument executes a rotating, reciprocating and/or vibrating working movement,
- a length measuring circuit portion disposed inside the handpiece and operable to transmit measuring signals for measuring length,
- a contact portion operable to establish a conductive path between the dental instrument serving as an electrode and the length measuring circuit portion, and
- an insulating portion that insulates the length measurement circuit portion and the contact portion, through which a voltage is applied during measurement, from the outer sleeve, wherein the outer sleeve does not conduct electricity during measurement, and
- wherein the contact portion comprises a contact device for use with a dental instrument having a conductive shaft, the contact device establishing a connection between the dental instrument and the length measuring circuit portion, and wherein the contact device comprises a conductive head spindle of the instrument carrier and at least one associated conductive gearwheel.

11. The handpiece of claim 10, wherein the insulating portion comprises a non-conductive supporting ring adjacent one end of the head spindle and a non-conductive socket adjacent an opposite end of the head spindle.

12. The handpiece of claim 10, wherein the insulating portion comprises at least one non-conductive rolling bearing for the head spindle.

13. The handpiece of claim 10, wherein the length measuring circuit portion comprises a conducting wire and the insulating portion comprises a wire sheath of non-conductive material.

14. The handpiece of claim 10, wherein the insulating portion comprises a plastic material such as PEEK or silicone, or a ceramic material such as silicon nitride, zirconium nitride or silicon carbide, or a coating comprised of said plastic material and/or said ceramic material and wherein the outer sleeve is made of a metallic material.

15. The handpiece of claim 10, wherein the length measuring circuit portion comprises the at least one transmission element.

16. A handpiece for measuring root canal length, comprising:
- an outer sleeve that is substantially non-insulating and is substantially free of any insulating coating,
- a connecting device for coupling the handpiece to a control and evaluation unit, to a measuring circuit with a current source for measurement of root canal length and to a drive unit,
- an instrument carrier configured to receive a dental instrument,
- at least one transmission element within the outer sleeve that transmits force to move the instrument carrier so that, when received in the instrument carrier, the dental instrument executes a rotating, reciprocating and/or vibrating working movement,
- a length measuring circuit portion disposed inside the handpiece and operable to transmit measuring signals for measuring length,
- a contact portion operable to establish a conductive path between the dental instrument serving as an electrode and the length measuring circuit portion, and
- an insulating portion that insulates the length measurement circuit portion and the contact portion, through which a voltage is applied during measurement, from the outer sleeve, wherein the outer sleeve does not conduct electricity during measurement,
- wherein the contact portion comprises a contact device for use with a dental instrument having a non-conductive shaft, the contact device establishing a connection between a conductive section of the dental instrument and the length measuring circuit portion, and wherein the contact portion is operable to connect a conductive section of the dental instrument received in the instrument carrier to the length measuring circuit portion via a conductive head spindle of the instrument carrier and at least one associated conductive gearwheel.

17. The handpiece of claim 16, wherein the insulating portion comprises a plastic material such as PEEK or silicone, or a ceramic material such as silicon nitride, zirconium nitride or silicon carbide, or a coating comprised of said plastic material and/or said ceramic material and wherein the outer sleeve is made of a metallic material.

18. A handpiece for measuring root canal length, comprising:
    an outer sleeve that is non-insulating and has no insulating coating;
    a connecting device for coupling the handpiece to a control and evaluation unit, to a measuring circuit with a current source for measurement of root canal length and to a drive unit;
    an instrument carrier configured to receive a dental instrument;
    at least one transmission element within the outer sleeve that transmits force to move the instrument carrier so that, when received in the instrument carrier, the dental instrument executes a rotating, reciprocating and/or vibrating working movement;
    a length measuring circuit portion disposed inside the handpiece and operable to transmit measuring signals for measuring length;
    a contact portion operable to establish a conductive path between the dental instrument serving as an electrode and the length measuring circuit portion; and
    an insulating portion that insulates the length measurement circuit portion and the contact portion, through which a voltage is applied during measurement, from the outer sleeve, wherein the outer sleeve does not conduct electricity during measurement, and
    wherein the length measuring circuit portion comprises the at least one transmission element.

19. The handpiece of claim 18, wherein the length measuring circuit portion comprises a conducting wire and the insulating portion comprises a wire sheath of non-conductive material.

20. The handpiece of claim 18, wherein the insulating portion comprises a plastic material such as PEEK or silicone, or a ceramic material such as silicon nitride, zirconium nitride or silicon carbide, or a coating comprised of said plastic material and/or said ceramic material and wherein the outer sleeve is made of a metallic material.

21. The handpiece of claim 18, wherein the insulating portion includes at least one of a coupling sleeve, a bearing sleeve, a spacer disk and a non-conductive rolling bearing.

22. A handpiece for measuring root canal length, comprising:
    an outer sleeve that is non-insulating and has no insulating coating;
    a connecting device for coupling the handpiece to a control and evaluation unit, to a measuring circuit with a current source for measurement of root canal length and to a drive unit;
    an instrument carrier configured to receive a dental instrument;
    at least one transmission element within the outer sleeve that transmits force to move the instrument carrier so that, when received in the instrument carrier, the dental instrument executes a rotating, reciprocating and/or vibrating working movement;
    a length measuring circuit portion disposed inside the handpiece and operable to transmit measuring signals for measuring length;
    a contact portion operable to establish a conductive path between the dental instrument serving as an electrode and the length measuring circuit portion; and
    an insulating portion that insulates the length measurement circuit portion and the contact portion, through which a voltage is applied during measurement, from the outer sleeve, wherein the outer sleeve does not conduct electricity during measurement, and
    wherein the insulating portion includes at least one of a coupling sleeve, a bearing sleeve, a spacer disk and a non-conductive rolling bearing.

23. The handpiece of claim 22, wherein the insulating portion comprises a plastic material such as PEEK or silicone, or a ceramic material such as silicon nitride, zirconium nitride or silicon carbide, or a coating comprised of said plastic material and/or said ceramic material and wherein the outer sleeve is made of a metallic material.

24. A handpiece for measuring root canal length, comprising:
    an outer sleeve that is substantially non-insulating and has no insulating coating,
    a connecting device for coupling the handpiece to a control and evaluation unit, to a measuring circuit with a current source for measurement of root canal length and to a drive unit,
    an instrument carrier configured to receive a dental instrument,
    at least one transmission element within the outer sleeve that transmits force to move the instrument carrier so that, when received in the instrument carrier, the dental instrument executes a rotating, reciprocating and/or vibrating working movement,
    a length measuring circuit portion disposed inside the handpiece and operable to transmit measuring signals for measuring length,
    a contact portion operable to establish a conductive path between the dental instrument serving as an electrode and the length measuring circuit portion,
    an insulating portion that insulates the length measurement circuit portion and the contact portion, through which a voltage is applied during measurement, from the outer sleeve,
    wherein the outer sleeve does not conduct electricity during measurement, and
    wherein the length measuring circuit portion extends from the head of the handpiece towards the connecting device and through at least a portion of the handpiece, and
    wherein the contact portion comprises at least one of a head spindle and an instrument carrier.

25. The handpiece of claim 24, wherein the length measuring circuit portion comprises at least one of a conducting wire and of the at least one transmission element.

26. The handpiece of claim 24, wherein the insulating portion comprises a plastic material such as PEEK or silicone, or a ceramic material such as silicon nitride, zirconium nitride or silicon carbide, or a coating comprised of said plastic material and/or said ceramic material and wherein the outer sleeve is made of a metallic material.

27. The handpiece of claim 24, wherein the insulating portion includes at least one of a coupling sleeve, a bearing sleeve, a spacer disk, a non-conductive rolling bearing and a wire sheath of non-conductive material.

* * * * *